United States Patent
Smith et al.

(10) Patent No.: US 6,846,291 B2
(45) Date of Patent: Jan. 25, 2005

(54) PRODUCTION OF LUBRICIOUS COATING ON ADHESIVE HYDROGELS

(75) Inventors: Larry L. Smith, Seattle, WA (US); Anthony M. Lowman, Wallingford, PA (US)

(73) Assignee: Sonotech, Inc., Bellingham, WA (US)

( * ) Notice: Subject to any disclaimer, the term of this patent is extended or adjusted under 35 U.S.C. 154(b) by 0 days.

(21) Appl. No.: 10/300,217

(22) Filed: Nov. 20, 2002

(65) Prior Publication Data

US 2004/0097807 A1 May 20, 2004

(51) Int. Cl.[7] ................................................. A61B 8/14
(52) U.S. Cl. .................................................... 600/459
(58) Field of Search ................................ 600/407, 437, 600/439, 438, 440, 441–459, 461–471; 73/625, 618, 626, 644; 128/916; 607/152; 601/2; 604/20, 22; 424/9.52, 9.51

(56) References Cited

U.S. PATENT DOCUMENTS 5,522,878 A * 6/1996 Montecalvo et al. ....... 600/459
6,039,694 A    3/2000 Larson et al.
6,478,739 B1 * 11/2002 Hong ......................... 600/437

* cited by examiner

*Primary Examiner*—Ali Imam
(74) *Attorney, Agent, or Firm*—Robert L. McDowell

(57) ABSTRACT

Method and formulations to extend the utility of ultrasound compliant adhesive hydrogel membranes from static to dynamic applications by modifying the surface of at least one face so as to transform the tactile nature of the surface from one that is adhesive and render it smooth and lubricious. Such modification thus provides one face that is smooth and lubricious and the other unmodified, hence providing one adhesive surface that can be attached to the skin of a patient, the face of an ultrasound probe or other surfaces that benefit from the adhesive/lubricious configuration of such modified adhesive hydrogels.

23 Claims, 2 Drawing Sheets

PRODUCTION OF LUBRICIOUS COATING ON ADHESIVE HYDROGELS

FIELD OF THE INVENTION

The present invention is directed to hydrogel membranes and specifically to surface modification of adhesive hydrogel membranes by application of glycols and polyglycols, which provides for creation of membranes wherein one side is lubricious and another side adhesive. Membranes so produced can be adjuncts to probes used for ultrasound medical diagnostic imaging, ultrasound therapy and non-destructive testing procedures.

BACKGROUND OF THE INVENTION

Material that is utilized to conduct ultrasound between an electronic device and a target body is commonly referred to as an ultrasound couplant, ultrasound gel, ultrasound transmission media or acoustic transmission media. Many fluids and water-based gels have been used as ultrasound couplants over the years. Early use of mineral oil, petroleum products and cellulose compounds were replaced by gels of water and acrylic based polymers such as CARBOPOL® (a registered trademark of Noveon, Inc.). Membranes having an adhesive quality were created for use as wound dressings, drug delivery, electrical conductivity and specialized medical devices. Many of these membrane formulations were based on derivatives of acrylic acid, humectants, cross-linkers, water, natural gums and other gel formers such as derivatives of alginic acid and other polysaccharides. U.S. Pat. No. 6,039,694 to Larson et al., teaches the application solid acoustic coupling membranes, consisting of hydrogels based on co-polymers of polyacrylonitrile. Membranes and acoustic coupling sheaths of Larson et al. are lubricious on both sides and throughout, and as such, cannot be adhesively attached to the face of the transducer or to the skin of the patient. This lubricity limits the use of these hydrogel membranes since general scanning requires that the probe move freely and in contact with the acoustic coupling as it is moved back and forth over the area of interest. When the smooth lubricious surface is in contact with the skin and the probe face is moved over the lubricious outer surface of the membrane, the membranes of this invention tend to slide with the ultrasound probe requiring subsequent repositioning of the membrane. The lubricious nature of these membranes further limit their usage to horizontal surfaces since in applications such as endarterectomy and breast biopsy, the membranes slide off the irregular surfaces.

Such membranes have utility in conducting ultrasound for medical applications and non-destructive testing. These applications utilize high frequency sound, typically between 0.5 and 20 MHz. Acoustic energy at such frequencies is poorly transmitted by air and requires a coupling or conduction medium similar in acoustic properties to tissue when used in medical diagnostic imaging and Non-Destructive Testing (NDT) applications. These acoustic coupling media have been commonly thick fluids, gels, or a media in solid form to transfer the acoustic energy between the target object and electronic devices. Ultrasound coupling media displace air and fills contours between the piezoelectric transducer or "eye" of the instrument, referred to in the industry as an ultrasound probe, which converts energy between electrical and acoustic, and the object of interest into and from which the acoustic energy is directed. This media by nature of its physical and acoustic properties, serves as an ultrasound acoustic coupler between the object and the electronic transducer, thereby acoustically joining the two, so that the ultrasound based information developed can freely pass back and forth between the object and the transducer.

Of recent development are biocompatible adhesive hydrogel membranes that are produced from formulations of polymers such as polyvinyl alcohol, polyvinylpyrrilidone (PVP), and polyethylene oxide (PEO) by cross-linking initiated by high-energy sources such as e-beam, gamma and ultraviolet radiation. The membranes are produced by casting polymer blends on a suitable backer, such as a polyethylene sheet, followed by high-energy irradiation, which cross-links the polymer blend to form a cohesive membrane that is flexible and adhesive throughout. Such cross-linked membranes are commonly formulated to be adhesive and hydrophilic, thus providing utility as wound dressings, cosmetic facial masks, and when impregnated with drugs; for example, hormones, anti-infective agents, analgesics, therapeutics and local anesthetics, can be used as agents for drug delivery. By addition of certain salts, i.e. potassium chloride, sodium chloride and magnesium acetate to the base formulations, the membranes can be made conductive and fabricated to form devices for physiological monitoring.

Such formulations also render these adhesive hydrogel membranes acoustically conductive, providing acceptable low levels of ultrasound impedance and artifact with excellent ultrasound transmission, thus creating membranes that can perform as solid couplants, suitable for medical ultrasound imaging and ultrasound based therapy applications in place of gels, thickened liquids and couplants as are known in the art.

Since many hydrogel membranes are commonly adhesive on both sides and throughout, the ease and range of use of these materials is generally limited to static applications such as fetal monitoring or those in which the adhesive membrane is enclosed in a protective cover as a means of conducting acoustic energy from the active face of an ultrasound probe through the cover and into an external couplant. The characteristic of adhesivity on all faces and throughout the hydrogel membrane limits its use with ultrasound probes by restricting free motion of the probe over the surface of the membrane such as when a membrane is placed on the skin as a coupling media or when attempting insertion of a membrane covered probe face into protective covers as is common procedure when used during surgery and intracavity examinations.

An advantage of the device of the present invention is that the above impediments caused by the adhesive nature of the external surface, as is present when its use is so configured such that the membrane is attached to the active face of an ultrasound probe or positioned on skin for ultrasound imaging and ultrasound based therapies, are substantially eliminated.

SUMMARY OF THE INVENTION

The present invention teaches a method of modifying the surface of adhesive hydrogels by application of glycols, preferably biocompatible glycols, including polyglycols, such as polyethylene glycol (PEG), propylene glycol, glycerin, polyglycol co-polymers and polyols to form surfaces that are smooth and lubricious. In such case, where one side of the adhesive hydrogel membrane is treated with these compounds to create such smooth and lubricious surface, the opposite face of the membrane remains adhesive. The addition of glycols to the adhesive hydrogel surface results in hydrogen bonding between the polymers and renders a surface that is lubricious. For example, addition of PEG to the surface of an adhesive polyvinylpyrrilidone (PVP) membrane results in hydrogen bonding between the polymers. This hydrogen bonding results in the formation of a lubricious gel surface.

In one application of the inventive device, the adhesive side of the hydrogel membrane can be attached as an adjunct to the active face of an ultrasound probe and/or also a greater portion of the probe. When so attached, and tightly conformed to the active face of the probe, the adhesive hydrogel self-couples acoustic energy into and out of itself and the external smooth and lubricious surface created by such treatment provides for dynamic motion of the probe over the skin or object, or within, such as when used for intracavity exams. In another application of the invention, the adhesive side of hydogel ultrasound coupling membrane is placed on the skin over an area of the body to be imaged, such as an endarterectomy wound.

DETAILED DESCRIPTION OF THE PREFERRED EMBODIMENT

In commercial production are hydrogel membranes that due to their chemical formulations and processing parameters are adhesive throughout. For example, adhesive hydrogel membranes based on Polyethylene oxide/ polyvinylpyrrilodone (GKG-1), Polyvinylpyrrilodone (GPPG-1) and a conductive adhesive hydrogel (RG 63B), all commercially available from Ludlow Technical Products, were utilized as starting material for the present invention. The PEO/PVP and PVP adhesive hydrogel membranes were cross-linked by E-beam radiation whereas the conductive hydrogel, generally used for physiological monitoring, was cross-linked by ultraviolet radiation. By virtue of their chemical composition, all of the above adhesive hydrogel membranes are biocompatible and acoustic self-coupling, having acceptable low levels of artifact and distortion.

Polyethylene glycols with molecular weights of 200 and 8000 daltons were applied to observe their surface modification potential. Union Carbide's Sentry Grade WSR N-10 polyethylene oxide, with a nominal molecular weight of 100,000 daltons was also used for polyglycols of the present invention.

Figure 1:
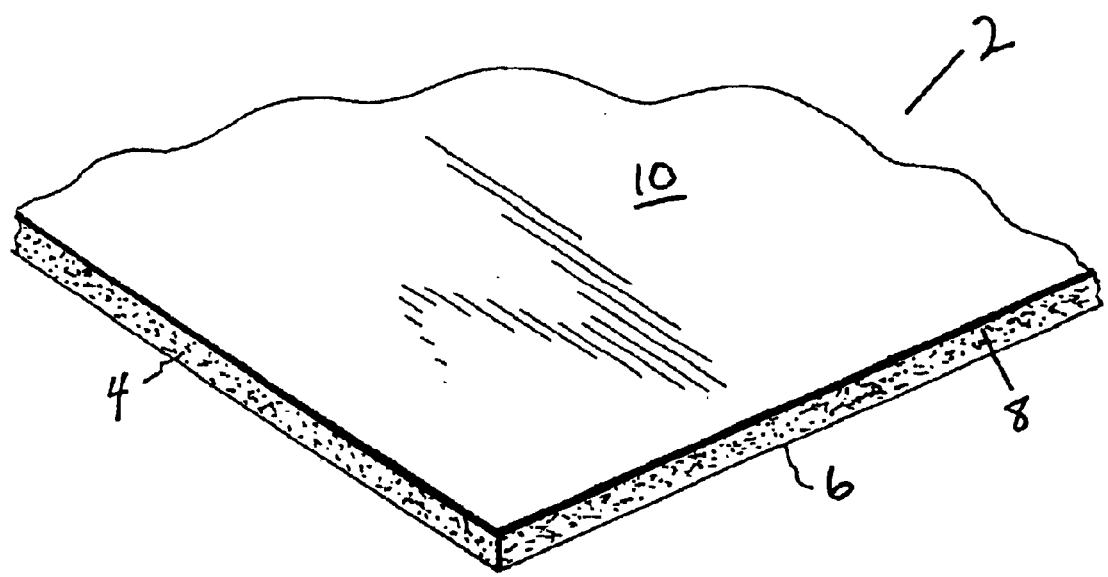
FIG. 1 illustrates the inventive coated hydrogel membrane.

Test solutions of PEG with molecular weights of 200, 4600 and 8000 with concentrations varying between 10 and 100% by weight, plus polyethylene oxide Grade N-10 (Union Carbide's Sentry Grade WSR N-10), propylene glycol, glycerin and water were used for evaluation of surface modification potential. The test solutions were applied to the surface of adhesive hydrogel membranes to determine effectiveness in modification of adhesive hydrogel surfaces, from tacky and adhesive to smooth and lubricious. A smooth and lubricious surface was created by application of approximately 1 ml of the solutions and evenly distributed by swabbing. FIG. 1, or example shows a coated adhesive hydrogel membrane 2 of the present invention wherein an adhesive hydrogel membrane 4 having opposed surfaces 6 and 8 includes a lubricious coating 10 applied to surface 8.

The adhesive hydrogel membranes evaluated were nominally 0.20 mm in thickness and so constructed that the membrane which is adhesive throughout, is covered by a top and bottom liner of polyethylene or similar film, such that the adhesive surfaces are retained within and unexposed to the environment. Adhesive polymer samples consisting of 2"×2" squares of PEO/PVP (GKG-1), PVP (GPPG-1) and a conductive membrane (RG-63B) were prepared by cutting from 8" widths of the respective polymers. The protective backing was removed from one side of the samples and coated with the above test solutions using a cotton swab. Application is not limited to swabbing and can include, spraying, brushing, dipping or any other suitable means of transferring a solution to the surface of the membrane. Observations regarding the adhesivity and lubricity of the surface were recorded at time points beginning with time of application and in subsequent 15-minute intervals for a period of 1 hour and in some cases, also after several days. Table 1, Table 2 and Table 3 are summaries of these observations.

TABLE 1

Surface Modification Characteristics of E-Beam Cured PEO/PVP GKG-1

| SOLUTION | 0 Minutes | 15 Minutes | 30 Minutes | 60 Minutes | 12 Days |
|---|---|---|---|---|---|
| WATER | S&L | T | T | T | T |
| PEG 200-100% | S&L | T | T | T | ST |
| PEG 200-50% | S&L | T | T | T | ST |
| PEG 4600-50% | S&L | ST | T | T | ST |
| PEG 8000-50% | S&L | S&L | S&L | S&L | ST |
| PEG 8000-25% | S&L | S&L | ST | ST | ST |
| PEG 8000-10% | S&L | T | T | T | ST |
| PEO N10-5% | S&L | S&L | ST | T | T |
| PEO N10-2.5% | S&L | T | T | T | T |
| GLYCERINE | S&L | T | T | T | ST |
| PROP GLYC | T | T | T | T | T |

S = Smooth,
L = Lubricious,
T = Tacky,
ST = Slightly Tacky

From Table 1 it can be concluded that molecular weight polyethylene glycols in the 200 to 8000 Dalton range demonstrate increasing surface modification effects as the molecular weight and concentration increase. For example, application of PEG 200 demonstrates a level of tack that after 15 minutes of contact is approximate to that of the untreated membrane. Propylene glycol and glycerin appear to react in a manner similar to PEG 200 as evidenced by a rapid decrease in gloss and increase in tack after application.

PEG's with molecular weights in the 200 to 4600 range do not appear to adequately modify the PEO/PVP adhesive hydrogel surfaces even when applied in undiluted form. When the molecular weight of the polyethylene glycol is increased to 8000, such as with Union Carbide Polyethylene Glycol 8000, PEG concentrations in water dilutions of 50% by weight form smooth lubricious surfaces on PEO/PVP adhesive hydrogels and can maintain such surfaces for a minimum of one hour which generally exceeds the time required for ultrasound examinations. Solutions of PEG 8000 in excess of 25% by weight are not easily sprayed; however, they can be effectively applied by a swab, brush, roller or other application mechanism.

TABLE 2

Surface Modification Characteristics of E-beam Cured PVP GPPG-1

| SOLUTION | 0 Minutes | 15 Minutes | 30 Minutes | 60 Minutes | 4 Days |
|---|---|---|---|---|---|
| WATER | S&L | T | T | T | T |
| PEG 200-100% | S&L | S&L | S&L | ST | ST |
| PEG 200-50% | S&L | T | T | T | T |
| PEG 4600-50% | S&L | S&L | S&L | S&L | S&L |
| PEG 8000-50% | S&L | S&L | S&L | S&L | S&L |
| PEG 8000-25% | S&L | S&L | ST | ST | T |
| PEG 8000-10% | S&L | S&L | S&L | ST | T |
| PEO N10-5% | S&L | ST | ST | T | T |
| PEO N10-2.5% | S&L | ST | ST | T | T |
| GLYCERINE | S&L | S&L | ST | ST | T |
| PROP GLYC | S&L | S&L | S&L | St | T |

S = Smooth,
L = Lubricious,
T = Tacky,
ST = Slightly Tacky

Based on the data obtained by treatment of PEO/PVP GKG-1 (Table 1) and PVP GPPG-1 (Table 2), samples of a UV cured adhesive hydrogel, (Ludlow RG-63B) were tested with water and the preferred polymer PEG 8000 at a concentration of 50% by weight. The data in Table 3 summarizes the data developed.

TABLE 3

Surface Modification Characteristics on UV Cured RG-63B

| SOLUTION | 0 Minutes | 15 Minutes | 30 Minutes | 60 Minutes |
|---|---|---|---|---|
| WATER | S&L | T | T | T |
| PEG 8000-50% | S&L | S&L | S&L | ST |
| PEG 8000-25% | S&L | S&L | ST | ST |
| PEG 8000-10% | S&L | ST | T | T |

S = Smooth,
L = Lubricious,
T = Tacky,
ST = Slightly Tacky

The RG-63B adhesive hydrogel membrane was treated with water and PEG 8000, the preferred polymer, at 10, 25 and 50% concentrations initially resulting in smooth and lubricious membrane surfaces for all the solutions. The lubricity initially created reverted to less preferred tacky surface conditions in time periods that varied with polymer concentration. As the PEG 8000 concentration increased, the time at which the membrane surface remained lubricious also increased, water being least effective in maintaining lubricity and PEG 8000 at a 50% concentration being the most effective. The study using the RG 63B adhesive hydrogel membrane was discontinued after one hour since all test items had reverted to a tacky or slightly tacky condition at this time point.

Comparison of the data in Tables 1, 2, and 3 show that all the test solutions applied to cross-linked PVP create smooth lubricious surfaces and maintain lubricity for a longer time period than that of the same solutions applied to cross-linked PEO/PVP and RG 63B adhesive membrane surfaces. The data developed indicates that a 50% solution of PEG 8000 is preferred compound and concentration for surface modification of PEO/PVP adhesive hydrogel sample, while 50% solutions of both PEG 4600 and 8000 are both effective in converting the adhesive membrane surfaces of the subject PVP hydrogels from adhesive to lubricious, with 50% solutions of PEG 8000 being the most preferred. All compounds tested appear to be more effective than water alone in converting the adhesive surfaces of the subject membranes to that of smooth and lubricious.

The modified surface subsequently maintains such smooth and lubricious surfaces for time periods in excess of time generally required to perform imaging such as in medical ultrasound. Polyethylene glycols, by nature of their structure and physiological interactions in vivo are biocompatible as indicated by their use in medical devices.

Figure 2:
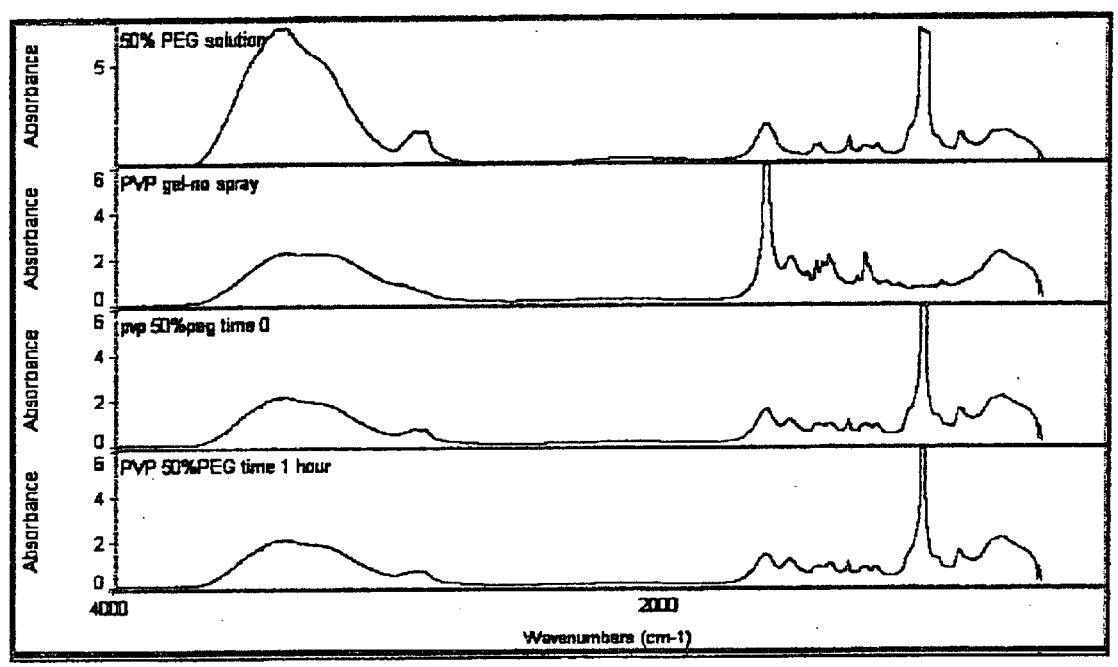
FIG. 2 shows FTIR analysis of PVP surfaces prior to and following the addition of PEG.

In order to characterize the nature of the modified surfaces created, FTIR (Fourier Transform Infrared Spectrophotometry) analysis of the PVP surfaces was performed prior to and following the addition of the PEG spray (PEG MW 8000, 50% concentration). As shown in FIG. 2, PEG is clearly present on the surface of the PVP following the addition of the spray. Furthermore, the PVP peak at approximately 1925 cm$^{-1}$ is shifted following the addition of PEG due to the hydrogen bonding. It is clear from the spectra that this bond exists up to at least 1 hour following administration.

To confirm the ultrasound coupling capability of the inventive adhesive hydrogel membranes, ultrasound imaging was performed in a clinical setting with an ATL HDI ultrasound-imaging instrument using an L10-5 probe. E-beam cross-linked PEO/PVP GKG-1, PVP GPPG-1 and UV cross-linked RG63B adhesive hydrogel membranes (as found in Tables 1–3 above) by Ludlow Technical Products were used in the evaluation. Imaging was first performed after attachment of the adhesive hydrogel membranes to the face of the probe followed by imaging through membranes adhesively attached to the skin of the patient. Lubricity of the membranes was accomplished by the application of water, or the indicated concentrations of PEG 4600, PEG 8000 and PEO N10 to the external surface of the adhesive hydrogel membranes which accommodated movement of the transducer over the target site and provided ease of insertion into a protective cover. Images produced by these methods were recorded on film. Images made with the inventive lubricious adhesive hydrogels were at least equivalent to the image quality of the same target site using commercially available transcutaneous coupling gels. The adhesive hydrogels provided as the above examples of this inventive device, are hydrophilic and therefore quickly absorbed water thus promoting the loss of lubricity and the return of adhesivity to the treated surface. Application of the subject polyethylene glycols retarded the reversion to tackiness of the smooth lubricious membrane surface.

The property of acoustic coupling provides utility for use of such membranes in ultrasound medical diagnostic imaging and therapies such as High Intensity Focused Ultrasound (HIFU) for producing heat or cautery, Lithotrypsy and transcutaneous ultrasound therapy, such as in Physical Therapy for soft tissue injury. In medical ultrasound imaging, a piezoelectric transducer, generally known in the industry as a probe, is placed in dynamic motion, commonly referred to as scanning, either in a configuration; wherein, the adhesive side of the modified membrane is attached to the active face of the probe exposing the smooth and lubricious surface, thus providing utility for dynamic movement of the probe in contact with the surface of the target; or whereby, the adhesive side of the hydrogel membrane is adhered to the subject being scanned and the ultrasound probe is dynamically moved over the smooth lubricious surface created by the device of this invention.

Although polyethylene glycols with molecular weights of between 200 and 8000 daltons and polyethylene oxide with a nominal molecular weight of 100,000 daltons are discussed above and reported in the Tables, the present invention is not limited thereto. Polyethylene glycols with molecular weights of up to at least 20,000 daltons and polyethylene oxide with nominal molecular weights about of up to at least 1,000,000 daltons are contemplated by the present invention. The glycols and polyglycols of the present invention may be in essentially pure form (allowing for any inevitable impurities) or may be in solution with water in concentrations of about 0.25 to about 99% by weight.

The method of the inventive device provides for creating a smooth lubricious surface by application of glycols, preferably polyethylene glycols to adhesive hydrogels, as previously described, that retain lubricity and functionality as solid ultrasound couplants that are tacky on one side and smooth and lubricious on the other.

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. An ultrasound acoustic coupling hydrogel membrane comprising a first adhesive side and a second adhesive side, said second adhesive side having a coating of at least one of glycols and polyglycols hydrogen bonded thereto said coating being lubricious.

2. The membrane of claim 1 wherein said at least one of glycols and polyglycols comprises polyethylene glycol.

3. The membrane of claim 2 wherein said polyethylene glycol has a molecular weight of up to 20,000 daltons.

4. The membrane of claim 3 wherein said polyethylene glycol has a molecular weight of 4800 to 8000 daltons.

5. The membrane of claim 4 wherein said polyethylene glycol has a molecular weight of 8000 daltons.

6. The membrane of claim 5 wherein said polyethylene glycol Is present in a solution further Including water, said solution comprising polyethylene glycol in a concentration of 50% by weight, the balance water.

7. The membrane of claim 1 wherein said at least one of glycols and polyglycols comprises polyethylene oxide.

8. The membrane of claim 7 wherein said polyethylene oxide has a molecular weight of up to 1,000,000 daltons.

9. The membrane of claim 1 wherein said at least one of glycols and polyglycols are biocompatible.

10. The membrane of claim 1 wherein said hydrogel membrane comprises one of (a) polyethylene oxide and polyvinylpyrrilodone, (b) polyvinylpyrrilodone or (c) a conductive hydrogel.

11. A method of producing an ultrasound acoustic coupling hydrogel membrane, said method comprising:
   providing a hydrogel membrane having a first adhesive side and a second adhesive side,
   contacting one of said first and second sides with at least one of glycols and polyglycols whereby a lubricious coating is formed that is hydrogen bonded to the contacted side.

12. The method of claim 11 wherein said at least one of glycols and polyglycols comprises polyethylene glycol.

13. The method of claim 12 wherein said polyethylene glycol has a molecular weight of up to 20,000 daltons.

14. The method of claim 13 wherein said polyethylene glycol has a molecular weight of 4800 to 8000 daltons.

15. The method of claim 14 wherein said polyethylene glycol has a molecular weight of 8000 daltons.

16. The method of claim 15 wherein said polyethylene glycol is present in a solution further including water, said solution comprising polyethylene glycol in a concentration of 50% by weight, the balance water.

17. The method of claim 11 wherein said at least one of glycols and polyglycols comprises polyethylene oxide.

18. The method of claim 17 wherein said polyethylene oxide has a molecular weight of up to 1,000,000 daltons.

19. The method of claim 11 wherein said at least one of glycols and polyglycols are biocompatible.

20. The method of claim 11 wherein the one contacted side remains lubricious for at least 15 minutes after said contacting.

21. The method of claim 11 wherein said at least one of glycols and polyglycols are in essentially pure form.

22. The method of claim 11 wherein said at least one of glycols and polyglycols are in solution with water in concentrations of 0.25 to 99%.

23. The method of claim 11 wherein said hydrogel membrane comprises one of (a) polyethylene oxide arid polyvinylpyrrilodone, (b) polyvinylpyrrilodone or (c) a conductive hydrogel.

* * * * *